United States Patent
Kleinekofort et al.

(10) Patent No.: US 8,180,443 B1
(45) Date of Patent: May 15, 2012

(54) DEVICE AND METHOD FOR MONITORING A PATIENT ACCESS, IN PARTICULAR A VASCULAR ACCESS IN EXTRACORPOREAL BLOOD TREATMENT

(75) Inventors: Wolfgang Kleinekofort, Kelkheim (DE); Andreas Wüpper, Büttelborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 500 days.

(21) Appl. No.: 12/440,951

(22) PCT Filed: Sep. 8, 2007

(86) PCT No.: PCT/EP2007/007849
§ 371 (c)(1),
(2), (4) Date: Mar. 12, 2009

(87) PCT Pub. No.: WO2008/031539
PCT Pub. Date: Mar. 20, 2008

(30) Foreign Application Priority Data

Sep. 12, 2006 (DE) .................. 10 2006 042 646

(51) Int. Cl.
*A61B 5/05* (2006.01)
(52) U.S. Cl. ....................................... 600/547
(58) Field of Classification Search .................. 600/300, 600/301, 481, 504–507, 547, 561, 573, 576, 600/579
See application file for complete search history.

(56) References Cited

U.S. PATENT DOCUMENTS

| | | |
|---|---|---|
| 6,932,786 B2 | 8/2005 | Giacomelli et al. |
| 7,060,047 B2 | 6/2006 | Lodi et al. |
| 2003/0195453 A1 | 10/2003 | Han et al. |
| 2003/0195454 A1 | 10/2003 | Wariar et al. |
| 2006/0081517 A1 | 4/2006 | Toyoda et al. |

FOREIGN PATENT DOCUMENTS

| | | |
|---|---|---|
| DE | 197 39 099 C1 | 1/1999 |
| DE | 10 2006 041265 B3 | 12/2007 |
| WO | 99/29356 | 6/1999 |
| WO | 03/086505 A | 10/2003 |
| WO | 2004/108206 A1 | 12/2004 |

OTHER PUBLICATIONS

International Search Report, PCT/EP2007/007849, mailed Jan. 16, 2008.
"Method for detecting the disconnection of an extracorporeal device using a patient's endogenous electrical voltages," Ross et al., Kidney International, 2006, 69: 2274-2277.

(Continued)

*Primary Examiner* — Jeffrey G Hoekstra
(74) *Attorney, Agent, or Firm* — Kenyon & Kenyon LLP (57) ABSTRACT

The present invention relates to a device and a method for monitoring a patient access, in particular a vascular access in extracorporeal blood treatment, in which a patient's blood is withdrawn from the patient via an arterial conduit and is returned to the patient via a venous conduit. The blood is conveyed by a blood pump, preferably an occlusive blood pump, such as a roller pump. To monitor the vascular access, the electrical AC voltage and/or the alternating current and/or a derived electrical measured variable that is generated by electrostatic charges during operation of the occlusive peristaltic pump is monitored. If the triboelectric AC voltage generated by the blood pump and/or the alternating current and/or the derived electrical measured variable lies within predetermined limits, this indicates that the vascular access is faulty.

17 Claims, 4 Drawing Sheets

OTHER PUBLICATIONS

"Study on causes and prevention of electrostatic charge build-up during extracorporeal circulation," Snijders et al., Perfusion, 1999, 14: 363-370.

"Investigation of the phenomenon of electrostatic compromise of a plastic fiber heat exchanger," R.J. Elgas, Perfusion 1999, 14: 133-140.

International Preliminary Report on Patentability for PCT/EP2007/007849, mailed on May 12, 2009.

DEVICE AND METHOD FOR MONITORING A PATIENT ACCESS, IN PARTICULAR A VASCULAR ACCESS IN EXTRACORPOREAL BLOOD TREATMENT

CROSS REFERENCE TO RELATED APPLICATIONS

This is a 371 national phase application of PCT/EP2007/007849 filed Sep. 8, 2007, claiming priority to German Patent Application No. 10 2006 042 646.0 filed Sep. 12, 2006.

FIELD OF INVENTION

The present invention relates to a device and a method for monitoring an access to a patient, in which a fluid is withdrawn from the patient via a first tubular conduit, which comprises a first patient connector, and the fluid is returned to the patient via a second tubular conduit, which comprises a second patient connector. In particular, the present invention relates to a device and method for monitoring a vascular access during an extracorporeal blood treatment in which a patient's blood is withdrawn from the patient via an arterial tubular conduit, which comprises an arterial patient connector with an arterial puncture cannula, and is returned to the patient via a venous tubular conduit, which comprises a venous patient connector with a venous puncture cannula.

BACKGROUND OF THE INVENTION

In the field of medical engineering, many devices are known with which fluids can be withdrawn from patients or delivered to the patients via a tubular conduit. The access to the patients is usually made with catheters for insertion into organs of the body, or with cannulas for puncturing vessels. During the examination or treatment, correct access to the patient has to be ensured. It is therefore necessary to monitor the patient access. In blood purification methods such as hemodialysis, hemofiltration and hemodiafiltration, a patient's blood is passed through an extracorporeal blood circuit which comprises a membrane filter, for example a dialyzer, or a hemofilter or hemodiafilter divided by a semipermeable membrane into a blood chamber and a separate dialysis fluid chamber or filtrate chamber via which the filtrate drains off. In a hemodiafiltration machine in which both hemodialysis and hemofiltration are performed simultaneously, the draining of filtrate also takes place at the same time on the dialysate side. If the venous connection to the patient comes loose during the blood treatment, bleeding to death can be avoided only if the extracorporeal blood flow is stopped within a few seconds. Therefore, the extracorporeal blood circuit of the known blood treatment devices is generally provided with protective systems which, in the event of an alarm, stop the blood pump, close the venous tube clamp and emit an acoustic and/or optical warning signal.

DE 197 39 099 C1 describes a device for monitoring a vascular access during an extracorporeal blood treatment, in which an electric current is induced in the connection of the extracorporeal blood circuit representing a closed conductor loop, the current flowing in the conductor loop is measured, and a characteristic change in the current strength points to a faulty vascular access. In addition to inductive injection and output, it is also known, from document U.S. Pat. No. 6,932,786 B2, to perform capacitive injection and output of electric signals in the extracorporeal blood circuit.

WO 99/29356 describes a device for monitoring a vascular access, with a puncture cannula to which a tubular conduit is connected that leads to a fluid source. For monitoring the vascular access, an electrical signal is injected into the fluid flow downstream of the fluid source, at a first location of the tubular conduit, and an electrical signal is output from the fluid flow at a second location downstream of the first location. The electrical signal, however, can also be output at a location on the patient's skin. If the output electrical signals are greater than a predetermined limit value, an alarm is triggered.

US 2003/0195454 A1 deals with the problem of capacitive injection and output of measurement signals in the extracorporeal blood circuit and proposes injection and output of the measurement signals by means of electrical contact elements that are in contact with the blood flowing through the tubular conduits.

US 2006/0081517 A1 discloses a device for monitoring the arterial and venous vascular access during an extracorporeal blood treatment with a hemodialysis device in which a predetermined voltage is applied to the dialysis fluid circuit and blood circuit. The voltage lies between two electrodes, of which one is in contact with the blood flowing in the blood circuit, and of which the other is in contact with the dialysis fluid flowing in the dialysis fluid circuit, so that there is an electric current flowing in the blood circuit and in the dialysis fluid circuit. The known device assumes that the peristaltic blood pump arranged in the blood circuit constitutes an interruption of the electric circuit.

The devices and methods described above have the disadvantage that electrical signals have to be injected into the fluids, as a result of which the outlay required for monitoring the patient access is increased. In addition, the injection of the electrical signals into the flow of fluid has proven problematic in many ways.

"Method for detecting the disconnection of an extracorporeal device using a patient's endogenous electrical voltages," by Ross et al. in *Kidney International* (2006) 69: 2274-2277 describes a method for monitoring a patient access in which electrical measurement signals are not injected into the flow of fluid, and instead it is only endogenous electrical voltages that are evaluated. The method by Ross et al. requires an electrical connection to be produced between two electrodes and the blood. The endogenous electrical signals that are picked up on the venous and arterial tubular conduits are almost identical because the measurement electrodes are at a distance measuring only a few centimeters. If the vascular access to the patient is as it should be, the difference of the measured signals is approximately zero. By contrast, in the case of a faulty vascular access, a potential difference can be demonstrated.

The known method is therefore based on monitoring the potential difference of endogenous signals, and the injection of electrical measurement signals into the flow of fluid is not necessary. However, a detection of ECG (electrocardiogram) signals with a voltage measurement at closely adjacent measurement points would be scarcely possible with the known method, because the so-called "heart vector" cannot be adequately recorded with such close spacing of the electrodes. For this reason, only diffuse endogenous signals could be detected by the measurement electrodes. During the measurement, interference signals from the environment are also inevitably measured, for example ripple voltages (50 Hz or 60 Hz) that are superposed on the supply voltage.

WO 2004/108206 A1 deals with the problem whereby occlusive blood pumps generate interference signals that are superposed on endogenous signals. This problem arises particularly when measuring ECG signals while the blood pump of an extracorporeal blood treatment device is running It is also known from WO 2004/108206 A1 that the dialyzer of a hemodialysis device does not constitute a barrier to an electric current flow between blood circuit and dialysis fluid circuit.

"Study on causes and prevention of electrostatic charge build-up during extracorporeal circulation," by Snijders et al. in Perfusion 1999; 14: 363-370 deals with the causes of the electrostatic charging in extracorporeal blood circuits and with their prevention, while "Investigation of the phenomenon of electrostatic compromise of a plastic fiber heat exchanger," R. J. Elgas, in Perfusion 1999; 14: 133-140, deals with the phenomenon of electrostatic charging in a heat exchanger with synthetic fibers.

SUMMARY OF THE INVENTION

It is an object of the present invention to provide a device that permits very reliable monitoring of the access to a patient, without external injection of measurement signals. It is a further object of the present invention to provide a blood treatment device that comprises a device permitting very reliable monitoring of the patient access without injection of measurement signals. It is also an object of the present invention to provide a method that permits very reliable monitoring of the access without injection of a measurement signal. The monitoring device according to the present invention and the monitoring method according to the present invention differ from the monitoring devices and monitoring methods known from the prior art in that the electrical signals which are required for the measurement, and which initiate a current in the fluid flowing in the tubular conduits, do not have to be externally injected, but instead are generated by the pump or pumps for conveying the fluid. Therefore, in the method according to the present invention and in the device according to the present invention, no external devices are needed for generating measurement signals, as a result of which the outlay in terms of equipment is reduced.

The "interference signals" known as triboelectric voltages, which are generated by the occlusive blood pump arranged in the extracorporeal blood circuit, can advantageously be used for detecting a needle disconnection and/or a needle dislocation of the venous and/or arterial puncture cannula, so that the disadvantages of the known methods, that are based on recording endogenous electrical signals, can be overcome.

A basic condition of the device according to the present invention and of the method according to the present invention is that the fluid is conveyed by one or more pumps that generate a triboelectric AC voltage. These are in particular the occlusive peristaltic pumps that are generally used in blood treatment devices. An occlusive pump is to be understood as a pump whose pump action is based on at least one constriction site or occlusion site moving along the elastic tube, that serves as pump chamber, and in this way displacing the enclosed fluid in the advance direction. The constriction or occlusion sites can be generated, for example, by rollers or fingers or the like. The occlusion of the pump tube segment leads to DC isolation of the electric circuit that is formed by the fluid flowing through the tubular conduits.

The method according to the present invention and the device according to the present invention thus make use of the phenomenon that is known by the term triboelectricity in peristaltic pumps. In peristaltic pumps, it is known that the rolls of the roller pump cause charge separations on the inner and outer surfaces of the tube. In occlusive roller pumps, the charge separations lead to electrical charges both on the outside of the tube and the rollers and on the inside of the tube, and the charges can flow off from the outside of the tube and the rollers since the outside of the tube and the rollers are generally grounded. Hitherto, however, the triboelectric voltages have been regarded only as disturbance factors.

As a result of the triboelectric voltage, a current flow forms in the fluid, with the pump functioning as voltage generator. In the event of a faulty vascular access, for example a disconnection of the arterial and/or venous cannula, the current flow is interrupted.

In the device according to the present invention and the method according to the present invention, the amplitude of the measured triboelectric AC voltage is monitored, and, if the amplitude of the measured voltage lies within predetermined limits, this points to a faulty vascular access. It is also possible, however, to measure the triboelectric alternating current or a derived electrical measured variable, for example the resistance.

In a preferred embodiment, the amplitude of the measured triboelectric AC voltage is compared to a predetermined limit value, and, if the amplitude of the AC voltage is greater than the predetermined limit value, this points to a faulty vascular access. It is also possible, in principle, to carry out a comparison with several predetermined limit values in order to be able to differentiate between different states.

To increase reliability, the amplitude of the AC voltage is compared to a predetermined limit value at different consecutive times. If the amplitude of the AC voltage is greater than the predetermined value for a predetermined number of measurements at different consecutive times, this points to a faulty vascular access. The greater the number of the consecutive measurements, the greater the reliability with which a faulty vascular access is detected. On the other hand, the greater the sensitivity, the smaller the number of measurements.

The degree of reliability of the measurement can be further enhanced if the frequency of the electrical AC voltage signal is measured and compared to the frequency of the rotor of the pump. In a roller pump, for example, the frequency of the AC voltage signal depends on the speed of rotation of the rotor and the number of rollers. It is possible to conclude that there is a faulty vascular access only when the frequency of the AC voltage and the frequency of the rotor of the peristaltic pump correlate with one another. Otherwise, it is assumed that it is not the triboelectric voltage that is measured, but another interference signal, which does not permit any conclusion to be drawn regarding a faulty vascular access.

In the blood treatment device according to the present invention and the method according to the present invention for monitoring the access during an extracorporeal blood treatment, the triboelectric AC voltage and/or the triboelectric alternating current and/or a derived electrical measured variable is monitored during operation of the pump on the basis of electrostatic charges.

In a preferred embodiment that describes a hemodialysis machine, the triboelectric AC voltage is measured between the patient's skin and the dialysis fluid flowing in the dialysis fluid circuit. It is therefore unnecessary to provide measurement points, which have proven critical in practice, on the arterial and/or venous puncture cannula or on the extracorporeal blood circuit. The triboelectric AC voltage is preferably measured between an electrical contact element, placed on the patient's skin, and another contact element that is in contact with the dialysis fluid flowing in the dialysis fluid circuit. This is possible because the dialysis fluid circuit is electrically connected to the blood circuit via the semi-permeable membrane of the dialyzer.

Analogously to this illustrative embodiment, the triboelectric voltage can also be measured in a hemofiltration machine or a hemodiafiltration machine between the patient's skin and the filtrate, because the filtrate side of the hemofilter or of the hemodiafilter is electrically connected to the blood circuit via the semi-permeable membrane. In principle, however, it is also possible, instead of measuring the potential relative to a reference electrode arranged on the patient, to measure the potential relative to ground, i.e. the operational ground of the blood treatment device.

A standardized ECG electrode, for example, can be used as an electrical contact element placed at any desired location on the surface of the patient's skin.

BRIEF DESCRIPTION OF THE DRAWINGS

An illustrative embodiment of the invention is explained in greater detail below with reference to the drawings, in which.

DETAILED DESCRIPTION OF THE DRAWINGS

Figure 1:
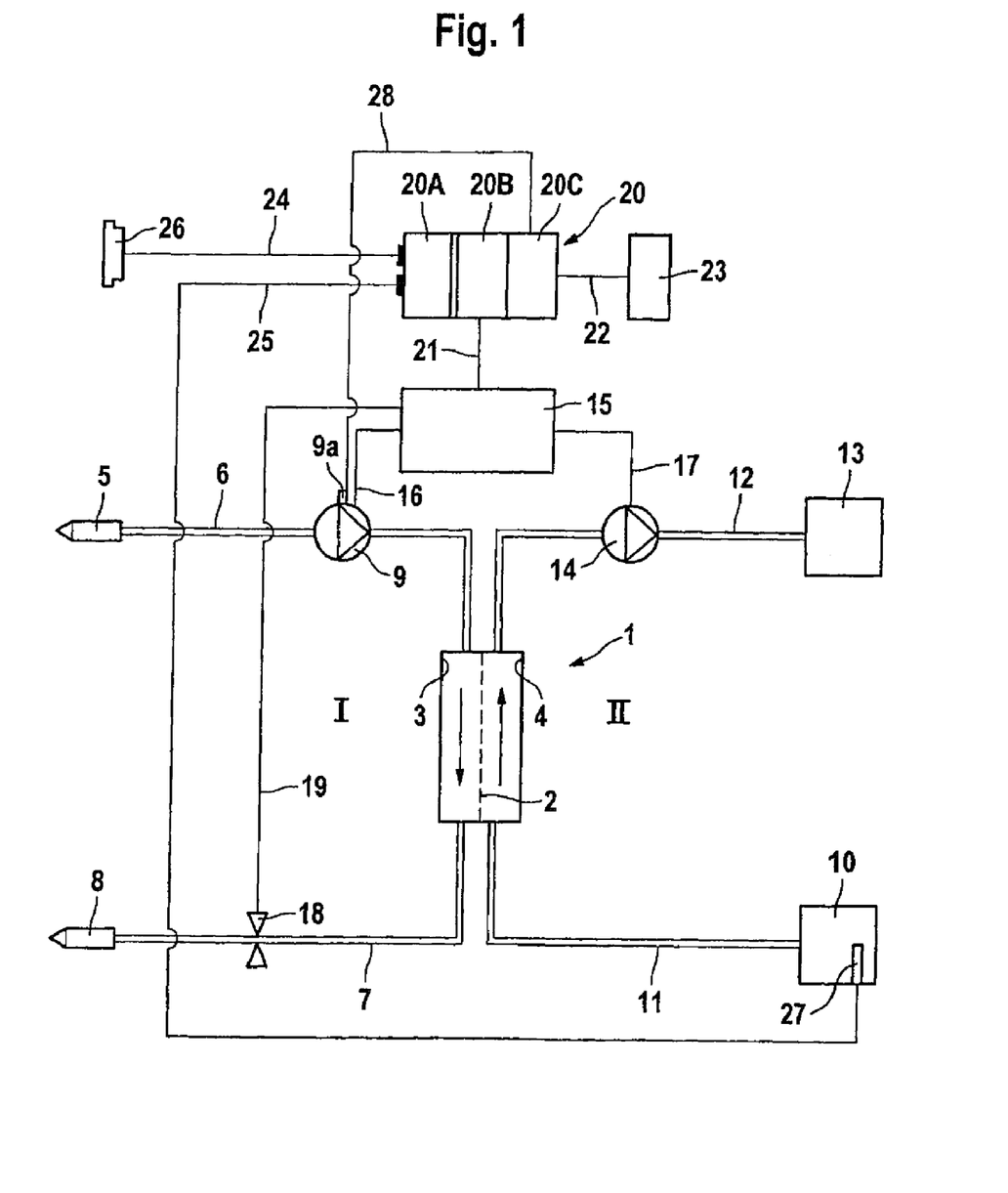
FIG. 1 shows the main components of a blood treatment device, together with a device for monitoring the patient access, in a greatly simplified schematic representation.

FIG. 1 shows the main components of a hemodialysis device, which comprises a device for monitoring the arterial and/or venous vascular access. The hemodialysis device has a dialyzer 1 which is divided by a semi-permeable membrane 2 into a blood chamber 3 and a dialysis fluid chamber 4. A flexible arterial tubular conduit 6 is connected to an artery of the patient by means of an arterial puncture cannula 5 and leads to the inlet of the blood chamber 3 of the dialyzer 1. Issuing from the outlet of the blood chamber 3 of the dialyzer 1, there is a flexible venous tubular conduit 7 which is connected to a vein of the patient by means of a venous puncture cannula 8. The arterial tubular conduit 6 is routed into an occlusive blood pump 9, in particular a peristaltic roller pump, which conveys the blood in the extracorporeal blood circuit I.

The dialysis fluid circuit II of the hemodialysis device comprises a dialysis fluid source 10 to which a dialysis fluid delivery line 11 is attached that leads to the inlet of the dialysis fluid chamber 4 of the dialyzer. Issuing from the outlet of the dialysis fluid chamber 4 of the dialyzer, there is a dialysis fluid discharge line 12 that leads to a drain 13. A dialysis fluid pump 14 is coupled into the dialysis fluid discharge line 12. In the case of hemofiltration, the "dialysis fluid chamber" represents a filtrate chamber 4 and the "dialysis fluid discharge line" represents a filtrate discharge line 12 via which the filtrate drains off.

The dialysis device is controlled by a central control unit 15 which regulates the blood pump 9 and dialysis fluid pump 14 via control lines 16, 17, respectively. Situated downstream of the blood chamber 3 of the dialyzer 1, on the venous tubular conduit 7, there is an electromagnetically activated tube clamp 18 which is closed via a further control line 19 from the central control unit 15 if the venous puncture cannula 8 (needle) slips out of the vascular access. In addition, the control unit 15 stops the blood pump 9 after the cannula has slipped out.

For monitoring the arterial and vascular access, the dialysis device comprises a monitoring device 20 which communicates with the control unit 15 via a data link 21. The monitoring device 20 is connected by a further data link 22 to an alarm unit 23 which, in the event of a faulty vascular access, for example a disconnection or a dislocation of the venous puncture cannula 8, emits an optical and/or acoustic alarm. Moreover, in the event of a faulty vascular access, the monitoring device prompts the central control unit 15, which then closes the venous tube clamp 18 and stops the blood pump 9.

The structure and mode of operation of the monitoring device according to the present invention are described below.

The monitoring device 20 comprises means 20A for measuring and filtering what in the present illustrative embodiment is an AC voltage with a very high-resistance input, to which a first electrical contact element 26 and a second electrical contact element 27 are connected via measurement lines 24, 25, respectively, an AC voltage being measured between these contact elements 26 and 27. The measurement range of the measurement unit 20A for the filtered measurement signal is between 0 and 2 V, preferably 0 to 1 V, and more particularly 0 to 500 mV. The unfiltered measurement signal has a level of about 7 V and can also assume higher values depending on the environmental conditions, because electronic appliances in the environment, especially in the home environment where electronic appliances are not shielded, can act as signal sources. The configuration values of the measurement unit 20A can therefore amount to 15 V, for example, or even 30 V. Values greater than 7 V may also occur for the filtered signal. When the device according to the present invention is implemented in a blood treatment device, a protective device is provided between the voltage meter and the patient in order to protect against transfer of overvoltages to the patient. This can be done, for example, by additional protective impedances, which leads to higher voltage values.

The first electrical contact element 26 is a conventional ECG electrode which is attached, for example, to the patient's wrist, while the second electrical contact element 27 is in electrical contact with the dialysis fluid, for example in the means 10 for preparation of the dialysis fluid, so that the electrical AC voltage generated by electrostatic charges during operation of the occlusive blood pump 9 can be measured.

To detect the triboelectric AC voltage, it would also be possible, in principle, to arrange a first electrode on the arterial blood conduit 6 and a second electrode on the venous blood conduit 7, these coming into contact with the blood flowing in the arterial or venous branch of the extracorporeal blood circuit I. However, contact of the blood with electrodes or the like should in principle be avoided. In addition, this would mean higher manufacturing costs for the tube set. By contrast, the device according to the present invention does without electrodes arranged in the arterial and venous branches of the extracorporeal circuit and proposes two electrical contact elements, of which one is applied to the patient's skin, and the other is in contact not with the blood, but with the dialysis fluid. The second electrical contact element can be any conductive element that is in contact with the dialysis fluid flowing in the dialysis fluid circuit. For example, the metal flanges of so-called Hansen connectors, or the electrodes of a level sensor arranged in the dialysis fluid circuit, can form the second electrical contact element.

The potential tap using the first electrical contact element 26 applied to the patient's skin is therefore made possible because the arterial puncture cannula 5 communicates conductively, via the vascular access, with the patient's cardiovascular system. The resistance R between the patient's vascular system and the skin surface is 1-2 MΩ, so that changes in potential within the vascular system can be detected directly on the skin. In principle, the position at which the first electrical contact element is placed on the patient's skin is not important.

Figure 2A:
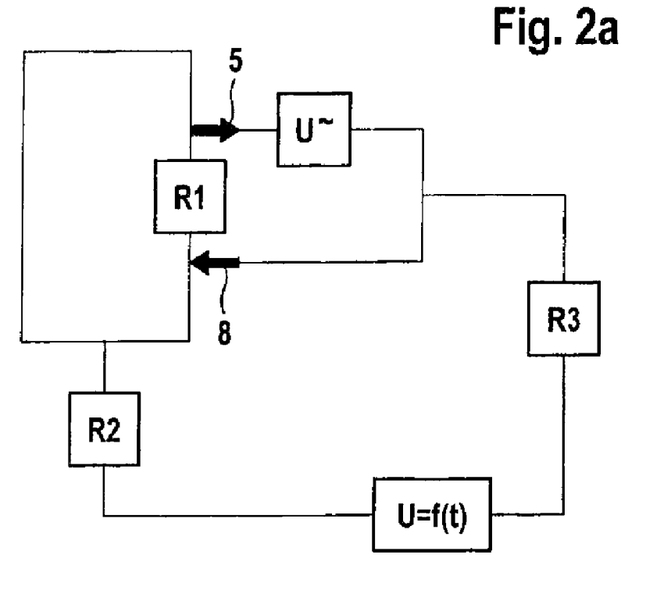
FIGS. 2a and 2b show equivalent circuit diagrams of the blood treatment device and of the patient when the vascular access is correct and when it is faulty, respectively.
Figure 2B:
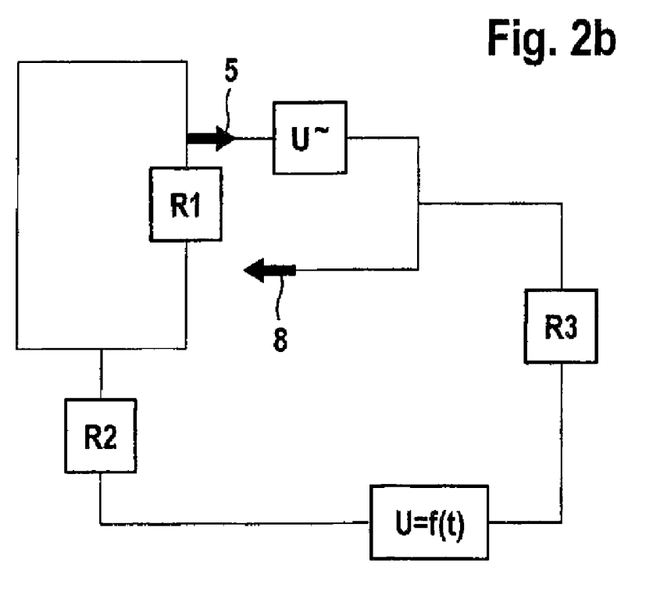

FIG. 2a shows a simplified equivalent circuit diagram of the patient and of the dialysis device. The occlusive blood pump 9 of the dialysis device is shown in the equivalent circuit diagram as generator U, which generates an AC voltage. R1 designates the resistance between arterial and venous puncture cannulas 5, 8. R2 is the resistance between the cardiovascular system and the skin surface, and R3 is the resistance between the second contact element 27 in the dialysis fluid circuit II and the dialyzer 1. In the simplified equivalent circuit diagram, the dialyzer, which has a negligible resistance, is not shown. To make things clearer, the resistances in the cardiovascular system are also not shown. The monitoring device 20 with the means 20A for measuring the time profile of the triboelectric AC voltage is designated by U=f(t). FIG. 2a shows the case in which both the arterial puncture cannula 5 and the venous puncture cannula 8 are correctly connected to the patient's vascular system. FIG. 2b shows the case in which the venous puncture cannula 8 has slipped out of the patient's vascular system. In other respects, FIGS. 2a and 2b are the same.

R1<<R2 in the case where there is a correct vascular access. Since only a negligible current flows through the measurement unit 20A, which has a very high-resistance input, the voltage generated by the occlusive blood pump 9 has the effect that a current flows through the resistance R1. Only very small voltage amplitudes are measurable between skin surface R2 and dialysis fluid circuit II.

By contrast, when the venous puncture cannula slips out of the vascular access (FIG. 2b), the resistance R1 between the arterial branch and the venous branch of the extracorporeal blood circuit I is infinitely great (R1>>R2), so that the triboelectric AC voltage generated by the blood pump 9 can be measured as potential difference between the skin surface and the dialysis fluid flowing in the dialysis fluid circuit II.

The dialysis device shown in FIG. 1, with the device for monitoring the vascular access, operates in the following way.

The measurement unit 20A of the monitoring device 20 measures, with the contact elements 26, 27, the potential difference between the skin surface of the patient and the dialysis fluid flowing in the dialysis fluid circuit II. The monitoring device 20 also comprises an evaluation unit 20B and 20C, which in turn comprises a comparison unit 20B for comparing the amplitude values A of the measured AC voltage to a predetermined limit value B(f), and a comparison unit 20C for comparing the rotor frequency of the blood pump 9 to the frequency f of the measured AC voltage. The comparison unit 20C is connected to the blood pump 9 via a line 28 so that the signal of the Hall sensor 9a integrated in the pump can be detected for determining the rotor frequency f of the pump. Since the amplitude of the measured AC voltage depends on the rotor frequency f of the blood pump, the predetermined limit value B(f) is chosen as a function of the rotor frequency f.

Figure 3:
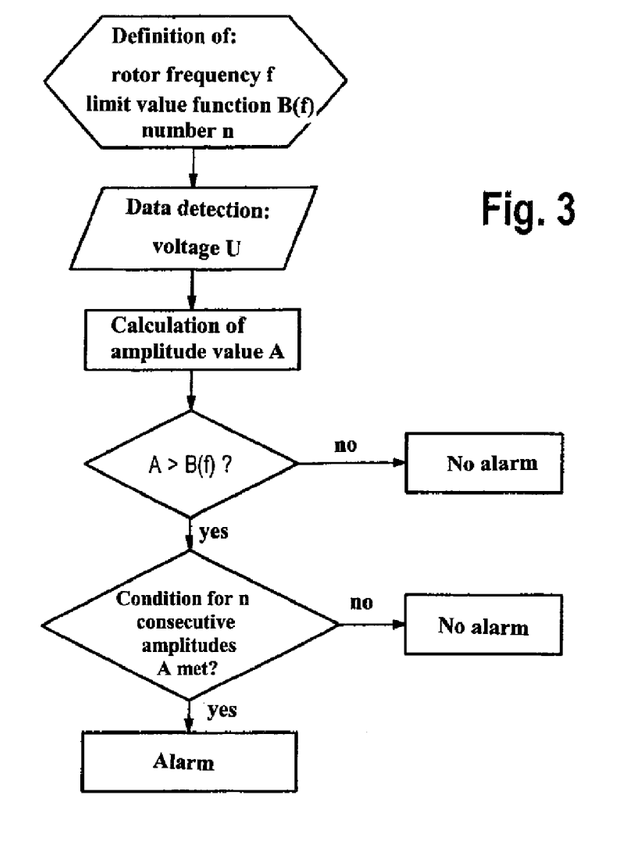
FIG. 3 shows a flowchart of the method according to the present invention.

FIG. 3 shows the flowchart for the evaluation of the measured signals. In the case where the values of the amplitudes of the measured AC voltage signal exceed the limit value B(f) for n consecutive amplitude values, the monitoring device 20 generates an alarm signal. After the alarm signal is generated, however, a faulty vascular access is assumed only when the rotor frequency of the blood pump 9 correlates with the frequency of the measured AC voltage signal. For this purpose, the comparison unit 20C compares both frequencies. If both frequencies are in a predetermined relationship to each other, which is dependent on the number of rollers of the roller pump 9, it is concluded that the measured signal is in fact the triboelectric voltage signal generated by electrostatic charges during operation of the blood pump, and not another "interference signal". Only in this case is it determined that a faulty vascular access is present and the alarm signal is sent to the alarm unit 23 and the central control unit 15, so that the alarm unit emits an acoustic and/or optical alarm and the control unit closes the venous tube clamp 18 and stops the blood pump 9.

Figure 4:
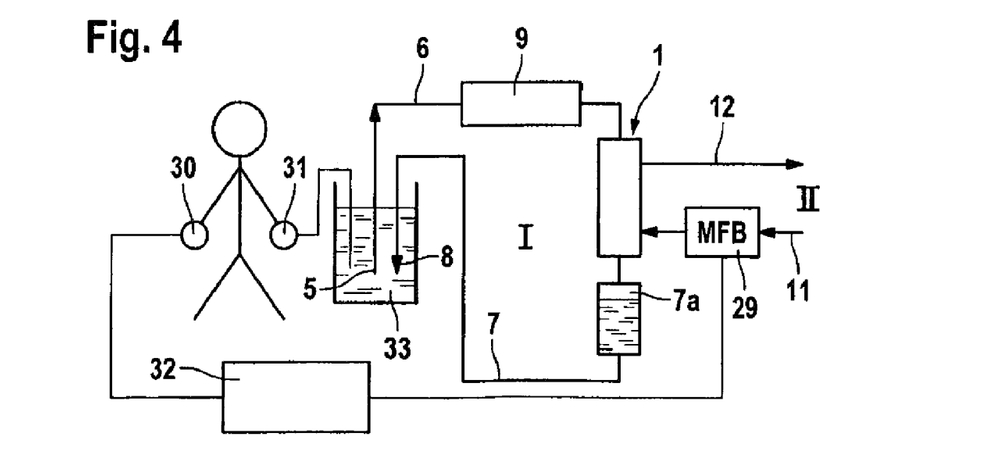
FIG. 4 shows a test set-up for simulation of the method according to the present invention.

The result of the measurement of the triboelectric AC voltage using an experimental test set-up is described below with reference to FIG. 4. Those parts of the test set-up that correspond to those parts of the dialysis device described with reference to FIG. 1 are provided with the same reference signs.

The test set-up comprises a dialyzer 1 with a blood circuit I and a dialysis fluid circuit II. The blood circuit I comprises an arterial blood conduit 6, in which an occlusive blood pump 9 is arranged, and a venous blood conduit 7 with a venous drip chamber 7a, while the dialysis fluid circuit II comprises a dialysis fluid delivery line 11 and a dialysis fluid discharge line 12. The dialysis fluid delivery line 11 runs through a multifunction block (MFB) 29 of the dialysis device used for the test purposes.

A test subject was fitted with ECG electrodes 30, 31 on the right and left forearms. One of the electrodes 30 was connected to measurement channel 1 of a voltage meter 32, while measurement channel 2 was connected directly to the dialysis fluid. For this purpose, the measurement channel 2 was connected by a cable to the contact plug of the level sensor on the multifunction block (MFB) 29. The second electrode 31 was connected via a cable to the dialysis fluid located in a beaker glass 33 that serves as reservoir for the dialysis fluid.

Dialysis fluid was used as blood substitute fluid. To maintain a conductive connection between electrode, cannula, tube set and dialyzer, the tube set was filled with physiological saline to the maximum level of the venous drip chamber 7a. The conductivity was 14.3 mS/cm. On the dialysate side, a standard dialysis fluid with identical conductivity was chosen. The arterial and venous puncture cannulas 5, 8 were located in the beaker glass 33. Standard tube sets and cannulas were used for all the tests.

Figure 5:
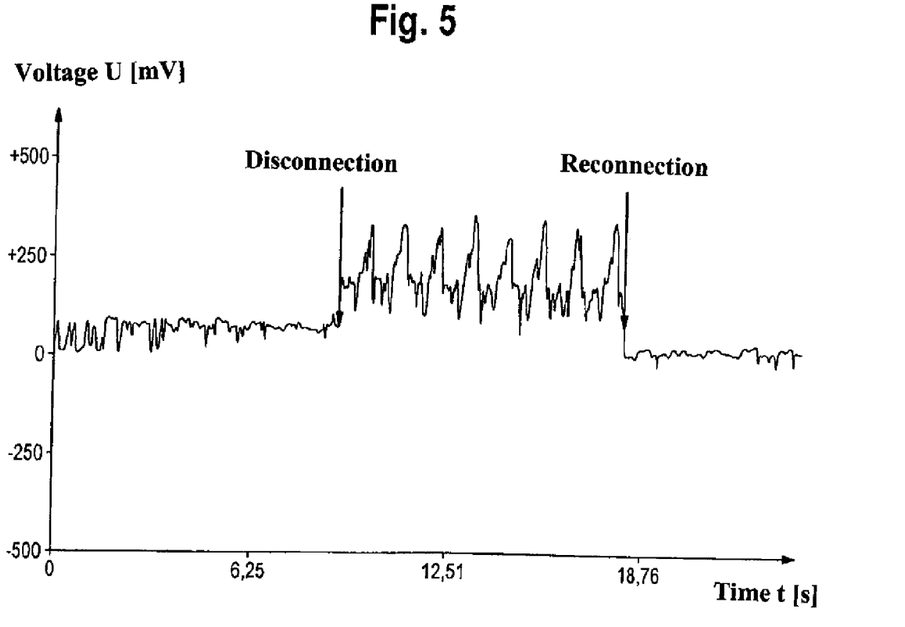
FIG. 5 shows the triboelectric voltage, measured in the test set-up of FIG. 4, as a function of time during a correct vascular access and a faulty vascular access.

FIG. 5 shows an example of the time profile of the voltage measurement between dialysis fluid circuit II and ECG electrode 30 on the test subject's wrist. The blood flow was 300 ml/min, and the dialysate flow was 300 ml/min. The venous cannula was then removed from the beaker glass. It will be seen that the signal changed without time delay. When the cannula was re-immersed into the beaker glass, the original signal was detected again.

The oscillation in the signal after venous disconnection corresponds to twice the frequency of rotation of the rotor of the blood pump. The data set was processed using an FIR low-pass filter with a cut-off frequency of 10 Hz. Test series were then carried out with variation of the blood flow and dialysate flow. A venous needle disconnection could be clearly detected in all test series with blood flows of between 100 ml/min and 600 ml/min and dialysate flows of 300, 500 and 800 ml/min.

The invention claimed is:

1. A device for monitoring vascular access during an extracorporeal blood treatment, in which a patient's blood is withdrawn from the patient via an arterial tubular conduit comprising an arterial patient connector with an arterial puncture cannula, the patient's blood is returned to the patient via a venous tubular conduit comprising a venous patient connector with a venous puncture cannula, and the blood is conveyed by a pump in the arterial tubular conduit or the venous tubular conduit that generates triboelectric charges during operation, the device comprising:
    a first contact element adapted to be placed on a patient's skin to produce an electrical connection to the patient's skin, and a second contact element adapted to be in contact with a fluid flowing in a dialysis fluid circuit or a fluid flowing in a filtrate fluid circuit;
    a measurement unit configured to measure at least one of: an AC voltage, an alternating current, and a derived electrical variable, each resulting only from the triboelectric charges generated by the pump, wherein the AC voltage, the alternating current, or the derived electrical variable is measured between the first contact element and the second contact element; and
    an evaluation unit configured to evaluate the at least one of: the measured AC voltage, the measured alternating current, and the measured derived electrical variable, wherein when there is a change in an amplitude of the at least one of: the measured AC voltage, the measured alternating current, and the measured derived electrical variable, this is a first indication of an incorrect vascular access.

2. The device of claim 1, wherein the evaluation unit comprises: a first comparison unit configured to compare the at least one of: the amplitude of the measured AC voltage, the amplitude of the measured alternating current, and the amplitude of the measured derived electrical variable, to a respective predetermined limit value,
    wherein the change in the amplitude comprises at least one of: the amplitude of the measured AC voltage, the amplitude of the measured alternating current, and the amplitude of the measured derived electrical variable, being greater than the respective predetermined limit value.

3. The device of claim 2, wherein the comparison unit is configured to compare the amplitude to the respective predetermined limit value at multiple consecutive times,
    wherein when the amplitude is greater than the respective predetermined limit value for a predetermined number of measurements at multiple consecutive times, this is a second indication of an incorrect vascular access.

4. The device of claim 1, further comprising:
    a sensor configured to measure a frequency of a rotor of the pump;
    wherein the evaluation unit further comprises: a second comparison unit configured to determine a frequency of the at least one of: the measured AC voltage, the measured alternating current, and the measured derived electrical variable; and configured to compare the measured frequency of the rotor of the pump to the at least one of: the frequency of the measured AC voltage, the frequency of the measured alternating current, and the frequency of the measured derived electrical variable,
    wherein when the frequency of the at least one of: the measured AC voltage, the measured alternating current, and the measured derived electrical variable correlates with the frequency of the rotor, this is a third indication of an incorrect vascular access.

5. The device of claim 4, further comprising:
    an alarm that is activated when there is at least one of: the first indication, the second indication, and the third indication of an incorrect vascular access.

6. The device of claim 1, wherein the pump is an occlusive peristaltic pump.

7. The device of claim 1, wherein the measurement unit is configured to measure the derived electrical variable, and the derived electrical variable is a resistance.

8. A blood treatment device comprising:
    at least one of: a dialysis fluid circuit comprising a dialyzer divided by a semi-permeable membrane into a blood chamber and a dialysis fluid chamber, and a filtrate fluid circuit comprising a membrane filter divided by a semi-permeable membrane into a blood chamber and a filtrate chamber;
    an extracorporeal blood circuit comprising:
        an arterial blood conduit connected to an inlet of the blood chamber and to an arterial puncture cannula for a vascular access, and
        a venous blood conduit connected to an outlet of the blood chamber and to a venous blood cannula for the vascular access; and
    the device for monitoring vascular access of claim 1.

9. The blood treatment device of claim 8, further comprising:
    a dialysis fluid preparation device,
    wherein the second contact element is in contact with the dialysis fluid in the dialysis fluid preparation device.

10. A method for monitoring the vascular access during an extracorporeal blood treatment, in which a patient's blood is withdrawn from the patient via an arterial tubular conduit comprising an arterial patient connector with an arterial puncture cannula, and the patient's blood is returned to the patient via a venous tubular conduit comprising a venous patient connector with a venous puncture cannula, the method comprising:
    conveying the blood in the arterial conduit or the venous conduit by a pump;
    generating triboelectric charges by operation of the pump;
    placing a first contact element on a patient's skin to produce an electrical connection to the patient's skin;
    contacting a second contact element with a fluid flowing in a dialysis fluid circuit or a fluid flowing in a filtrate fluid circuit;
    measuring at least one of the following: an AC voltage, an alternating current, and a derived electrical variable, each resulting only from the triboelectric charges generated by the pump, wherein the AC voltage, the alternating current, or the derived electrical variable is measured between the first contact element and the second contact element;
    evaluating the at least one of: the measured AC voltage, the measured alternating current, and the measured derived electrical variable; and
    determining there is a first indication of an incorrect vascular access when there is a change in an amplitude of the at least one of: the measured AC voltage, the measured alternating current, and the measured derived electrical variable.

11. The method of claim 10, further comprising:
    comparing the amplitude of the at least one of: the measured AC voltage, the measured alternating current, and the measured derived electrical variable, to a respective predetermined limit value; and
    wherein the change in the amplitude comprises at least one of: the amplitude of the measured AC voltage, the amplitude of the measured alternating current, and the amplitude of the measured derived electrical variable being greater than the respective predetermined limit value.

12. The method of claim 11, further comprising:
    comparing the amplitude at multiple consecutive times; and determining there is a second indication of an incorrect vascular access if the amplitude is greater than the respective predetermined limit value for a predetermined number of measurements at multiple consecutive times.

13. The method of claim 10, further comprising:
determining a frequency of the at least one of: the measured AC voltage, the measured alternating current, and the measured derived electrical variable;
comparing the frequency of a rotor of the pump to the at least one of: the frequency of the measured AC voltage, the frequency of the measured alternating current, and the frequency of the measured derived electrical variable; and
determining there is a third indication of an incorrect vascular access if the frequency of the at least one of: the measured AC voltage, the measured alternating current, and the measured derived electrical variable correlates to the frequency of the rotor.

14. The method of claim 13, further comprising:
activating an alarm following at least one of: the first indication, the second indication, and the third indication of an incorrect vascular access.

15. The method of claim 13, further comprising:
activating an alarm following the first indication, the second indication, and the third indication of an incorrect vascular access.

16. The method of claim 10, further comprising measuring the derived electrical variable, wherein the derived electrical variable is a resistance.

17. The method of claim 10, wherein the pump is an occlusive peristaltic pump.

* * * * *